(12) United States Patent
Cheng et al.

(10) Patent No.: US 11,278,415 B2
(45) Date of Patent: Mar. 22, 2022

(54) KNEE JOINT STRUCTURE

(71) Applicant: Ken Dall Enterprise Co., Ltd., New Taipei (TW)

(72) Inventors: Chia-Pao Cheng, New Taipei (TW); Chih-Hsuan Liang, New Taipei (TW); Hsiang-Ming Wu, New Taipei (TW)

(73) Assignee: KEN DALL ENTERPRISE CO., LTD., New Taipei (TW)

( * ) Notice: Subject to any disclaimer, the term of this patent is extended or adjusted under 35 U.S.C. 154(b) by 237 days.

(21) Appl. No.: 16/785,667

(22) Filed: Feb. 10, 2020

(65) Prior Publication Data
US 2021/0244544 A1 Aug. 12, 2021

(51) Int. Cl.
*A61F 2/38* (2006.01)
*A61F 2/30* (2006.01)
*A61F 2/46* (2006.01)

(52) U.S. Cl.
CPC ........ *A61F 2/38* (2013.01); *A61F 2002/3007* (2013.01); *A61F 2002/30329* (2013.01); *A61F 2002/30535* (2013.01); *A61F 2002/30624* (2013.01); *A61F 2002/4688* (2013.01)

(58) Field of Classification Search
CPC .................... A61F 2/38; A61F 2002/30624
See application file for complete search history.

(56) References Cited

U.S. PATENT DOCUMENTS

| | | | | |
|---|---|---|---|---|
| 6,629,999 B1 * | 10/2003 | Serafin, Jr. | .............. | A61F 2/384 623/20.15 |
| 2014/0236307 A1 * | 8/2014 | Whiteside | ............... | A61F 2/385 623/20.26 |
| 2017/0035572 A1 * | 2/2017 | Servidio | ................ | A61F 2/385 |

* cited by examiner

*Primary Examiner* — Jason-Dennis N Stewart
(74) *Attorney, Agent, or Firm* — Leong C. Lei

(57) ABSTRACT

A knee joint structure includes a knee joint head portion, a knee-joint body portion, and at least one curved plate. The knee joint head portion includes a position-returning device made up of a piston, an elastic body, and an adjustment cap and a transmission axle. The transmission axle includes a push-bar axle, which is pivotally coupled to a push bar operable to drive and move the piston. The knee-joint body portion includes a connection rod pivotally connected to the knee joint head portion. The curved plate connects the transmission axle and the knee joint body portion.

7 Claims, 14 Drawing Sheets

A-A
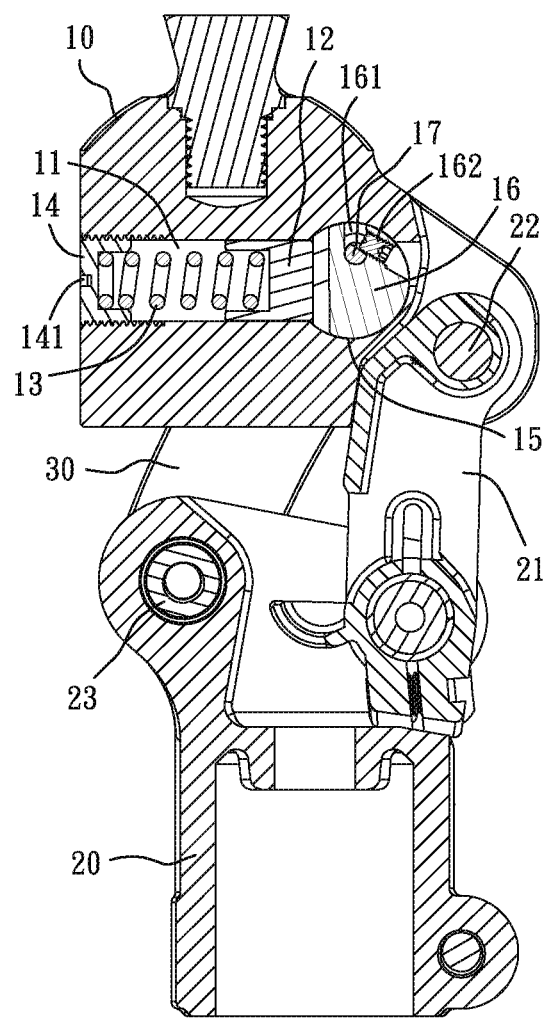
B-B
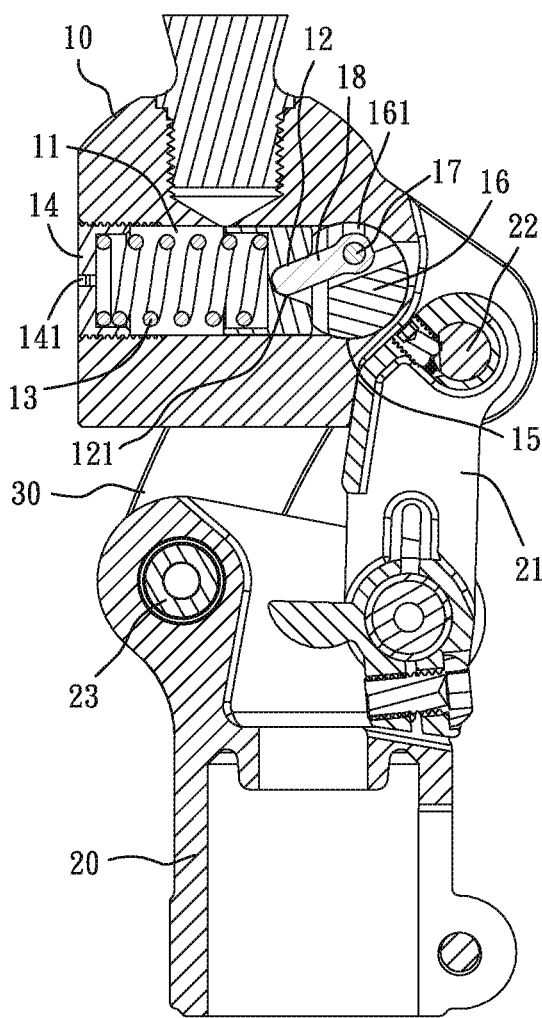
FIG. 5
FIG. 6

KNEE JOINT STRUCTURE

TECHNICAL FIELD OF THE INVENTION

The present invention relates to a knee joint structure, and more particularly to a knee joint structure of a prosthetic limb user that enhances walking safety, eases adjustment of joint restoration strength, and helps save effort required for walking.

DESCRIPTION OF THE PRIOR ART

A prosthetic limb is an artificially made limb that functionally replaces a damaged limb or aesthetically repairs the outside appearing of the damaged limb. Among others, a knee joint is a key feature of the prosthetic limb, because it is concerned with gait and dynamic balance of walking in order to take the place of a natural knee joint in respect of the functions of supporting and walking.

A prior art knee joint structure, as shown in FIGS. 15 and 16, generally comprises a knee joint head portion 91, a knee-joint body portion 92, and a connection rod 93 and curved plates 94 that connect the knee-joint head portion 91 and the knee-joint body portion 92 together, wherein the knee-joint body portion 92 is provided with a position-returning device 921 and the connection rod 93 is formed with a protrusion block 931. With such a structural arrangement, when the knee joint bends, the protrusion block 931 compresses the position-returning device 921 to accumulate a spring force so that the knee joint, when rotating in an opposite direction, is caused by the spring force released from the position-returning device 921 to return an original state.

Referring to FIGS. 16-18, due to the structural arrangement that the position-returning device 921 is arranged on the knee joint body portion 92 and the protrusion block 931 is arranged on the connection rod 93, an axis the knee joint changes during movement, so that a critical angle of bending of the knee joint is approximately 60°-80° (see FIG. 16); however, an actual situation of walking is that when the knee joint undertake fast walking, the angle of bending would easily exceed the critical angle, making the knee joint that is supposed to return to a straight state undesirably further rotates (such as in the condition of bending shown in FIG. 17, the rotation directions of the knee joint head portion 91 and the knee-joint body portion 92, as indicated by arrows, are not in a direction toward a straight condition), making it not possible to achieve a normal walking gait so as to easily tip.

Further, due to the structural arrangement that the position-returning device 921 is arranged on the knee-joint body portion 92 and the protrusion block 931 is arranged on the connection rod 93, together with the knee joint body portion 92 being connected to a shank prosthesis, adjustment of the strength of the elastic body can only be carried out by first removing the shank prosthesis, and this causes inconvenience in adjusting the strength of the elastic body.

SUMMARY OF THE INVENTION

An objective of the present invention is to provide a knee joint structure that enhances walking safety and allows walking to be carried out with less effort.

To achieve the above objective, the present invention comprises a knee-joint head portion, a knee joint body portion, and at least one curved plate, wherein the knee joint head portion is formed with a position-returning bore, the position-returning bore receiving a piston, an elastic body, and an adjustment cap to arrange therein, the elastic body having two ends respectively supported on the piston and the adjustment cap, the knee joint head portion being formed with an axle hole, the axle hole receiving a transmission axle to arrange therein, the transmission axle being formed with a notch, the notch receiving a push-bar axle to arrange therein, the push-bar axle being pivotally connected to a push bar that is operable to drive and move the piston; the knee-joint body portion comprises a connection rod, the connection rod having an end that is pivotally connected, by a first shaft, to the knee joint head portion, the knee-joint body portion further comprising a second shaft; and the curved plate has two ends that are respectively connected to the transmission axle and the second shaft.

As such, when the knee joint bends, the push bar compresses the elastic body to accumulate a spring force, so that the knee joint, when rotating in an opposite direction, is returned to an original state by the spring force of the elastic body. By arranging a position-returning device and the push bar in the knee-joint head portion, a critical angle of bending of the knee joint of the present invention can be set to be greater than the maximum angle of bending of walking, and this could ensure each step accomplished in a normal walking gait. As such, the present invention helps improve the drawback of a prior art knee joint of easily exceeding the critical angle after bending, which makes the knee joint that is supposed to get to a straight state continuously bending and causing tipping and hurting, and therefore enhances safety of operation.

Further, the location for adjusting the strength of the elastic body is improved in order to allow adjustment of the strength to be carried out according to a walking speed of a user, allowing walking to be conducted with less effort.

BRIEF DESCRIPTION OF THE DRAWINGS

FIG. 5 is a cross-sectional view taken along line A-A.
FIG. 6 is a cross-sectional view taken along line B-B.
FIGS. 7 and 8 are cross-sectional views illustrating operation of the present invention, in which
FIG. 7 shows a bending angle in walking is in a range of approximately 60°-80°, the bending angle being less than a critical angle;
and FIG. 8 shows the knee bending angle is greater than 90° but is still less than the critical angle.

FIGS. 15-17 are cross-sectional views of a prior art device, in which FIG. 16 shows a walking gait having a bending angle less than 90°, but exceeding the critical angle; and FIG. 17 shows the knee joint is abnormally bending rearward.

DETAILED DESCRIPTION OF THE PREFERRED EMBODIMENT

Figure 1:
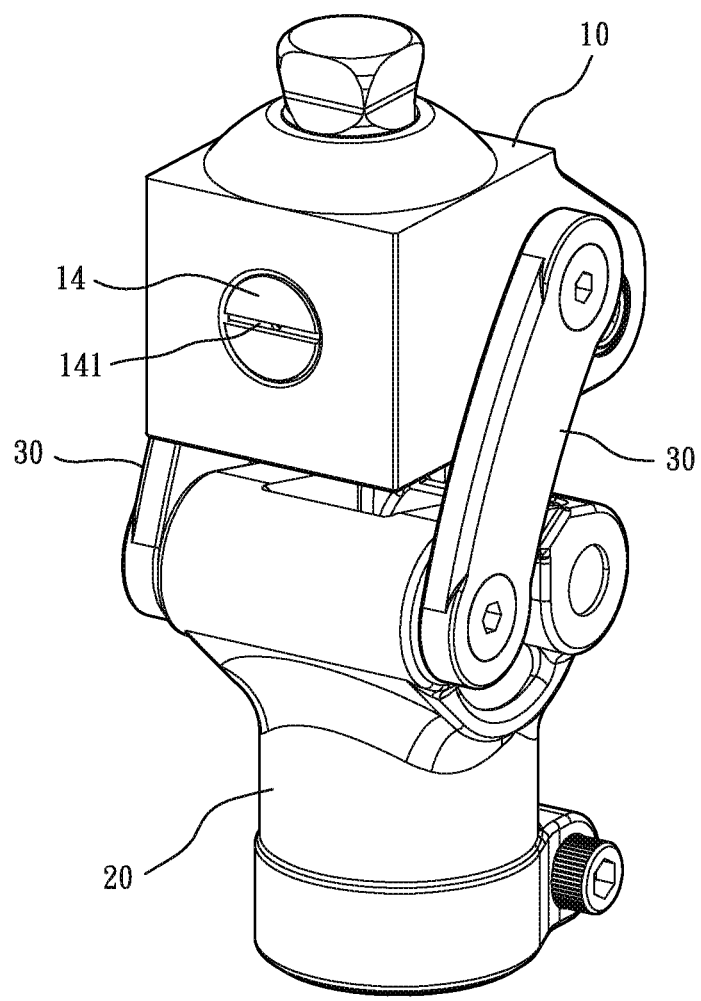
FIG. 1 is a perspective view of the present invention.
Figure 2:
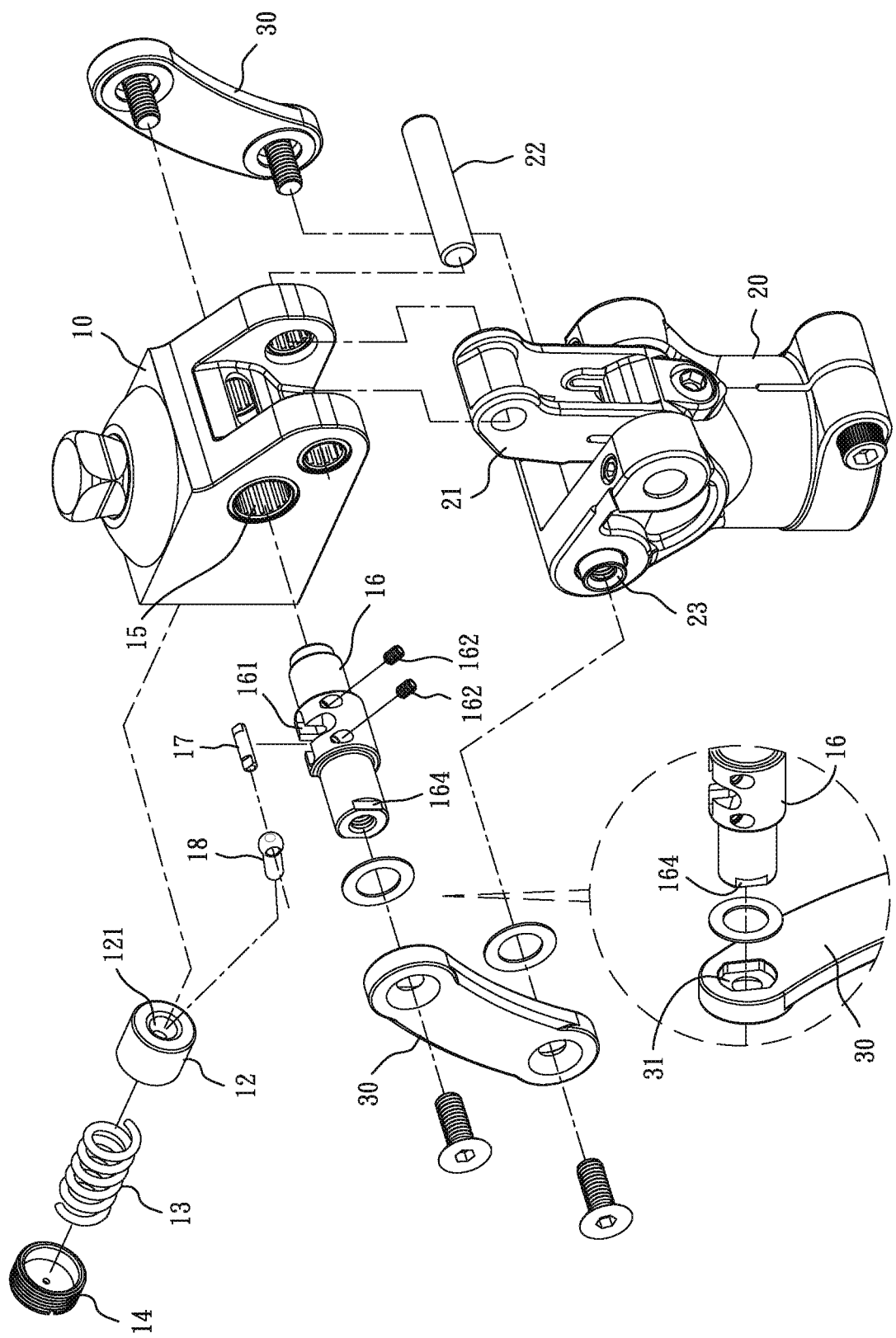
FIG. 2 is an exploded view of the present invention.
Figure 3:
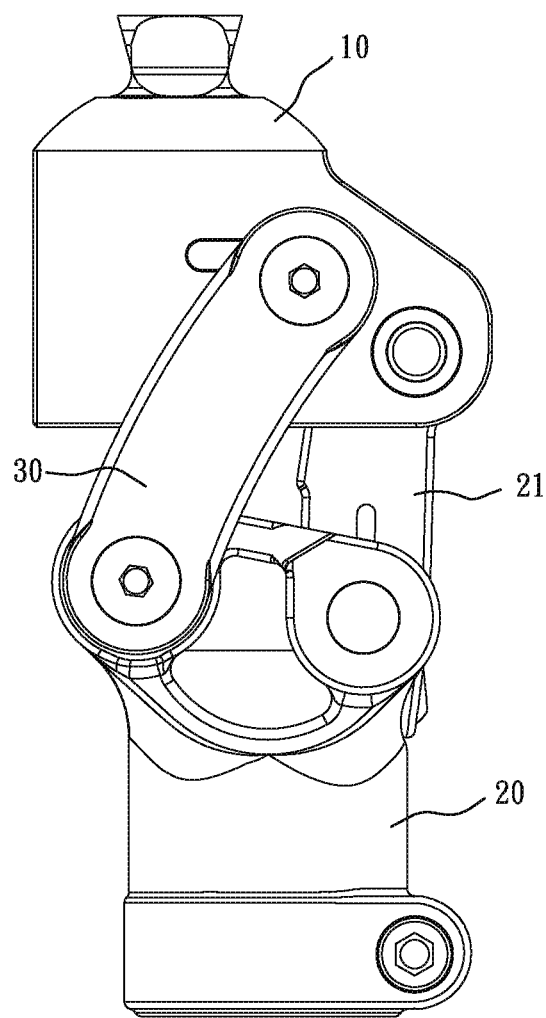
FIG. 3 is a right-side elevational view of the present invention.
Figure 4:
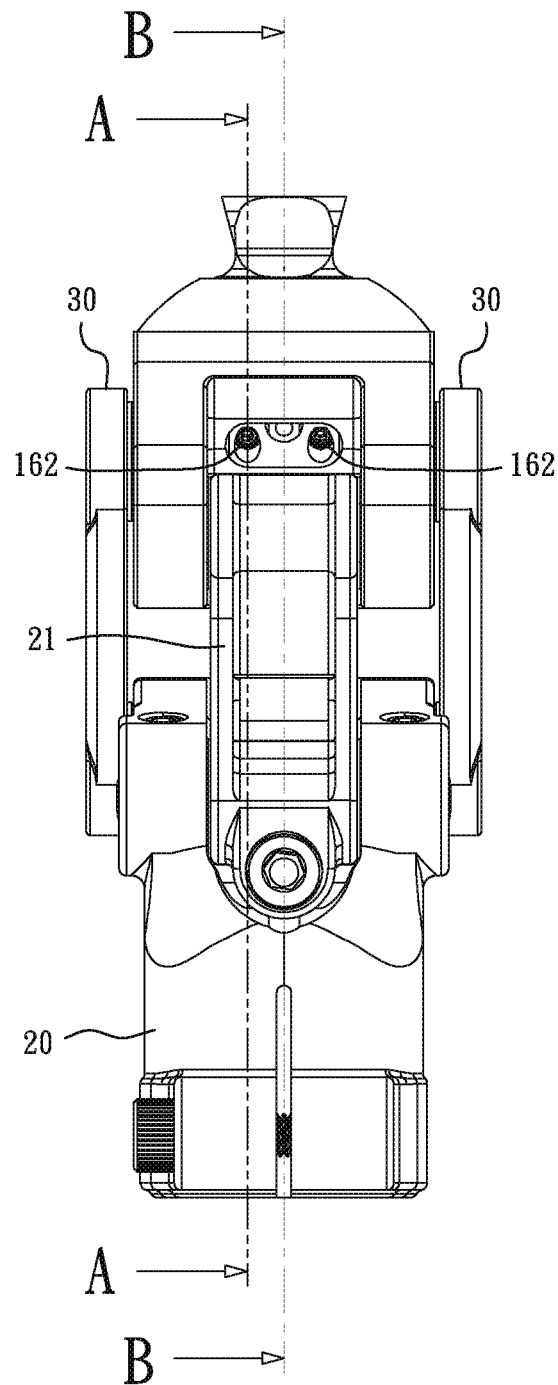
FIG. 4 is a rear view of the present invention.

Referring to FIGS. 1-6, the present invention comprises a knee-joint head portion 10, a knee-joint body portion 20, and two curved plates 30. A detailed description will be provided below:

The knee joint head portion 10 is formed with a position-returning bore 11. Arranged inside the position-returning bore 11 include a piston 12, an elastic body 13, and an adjustment cap 14. The elastic body 13 has two opposite ends respectively supported on the piston 12 and the adjustment cap 14. The knee joint head portion 10 is formed with an axle hole 15. The axle hole 15 receives a transmission axle 16 arranged therein. The transmission axle 16 is formed with a notch 161, and a push-bar axle 17 is arranged in the notch 161. The push-bar axle 17 pivotally couples a push bar 18 that is operable to push, drive, and move the piston 12.

The knee-joint body portion 20 includes a connection rod 21. The connection rod 21 has an end that is pivotally connected, by a first shaft 22, to the knee joint head portion 10. The knee joint body portion 20 further includes a second shaft 23.

The curved plates 30 each have two ends that are respectively connected to the transmission axle 16 and the second shaft 23.

In an embodiment, the piston 12 is formed with a cavity 121. An end of the push bar 18 is arranged to extend into and is contact engagement with the cavity 121 to achieve an effect of positioning, so that the push bar 18 can be stably set in the range of the cavity 121 to prevent pushing the piston 12 in a position-deviated manner.

In an embodiment, the transmission axle 16 is provided with bolts 162 extending therethrough so that ends of the bolts 162 are set in contact with the push-bar axle 17 to fix the push-bar axle 17 in the notch 161.

In an embodiment, the transmission axle 16 has an end having a surface that is formed with a flat section 164 so as to form an irregularly-shaped end configuration. The curved plate 30 is formed with a retaining engagement trough 31. The retaining engagement trough 31 is shaped to correspond to the irregular shape of the end configuration, so that the end of the transmission axle 16 is set in and in mating and retaining engagement with the retaining engagement trough 31 to achieve operative coupling between the curved plate 30 and the transmission axle 16.

The above provides a description of the components of the present invention and assembly thereof. In the following, an example of operation, as well as features and advantages, of the present invention will be described.

Figure 7:
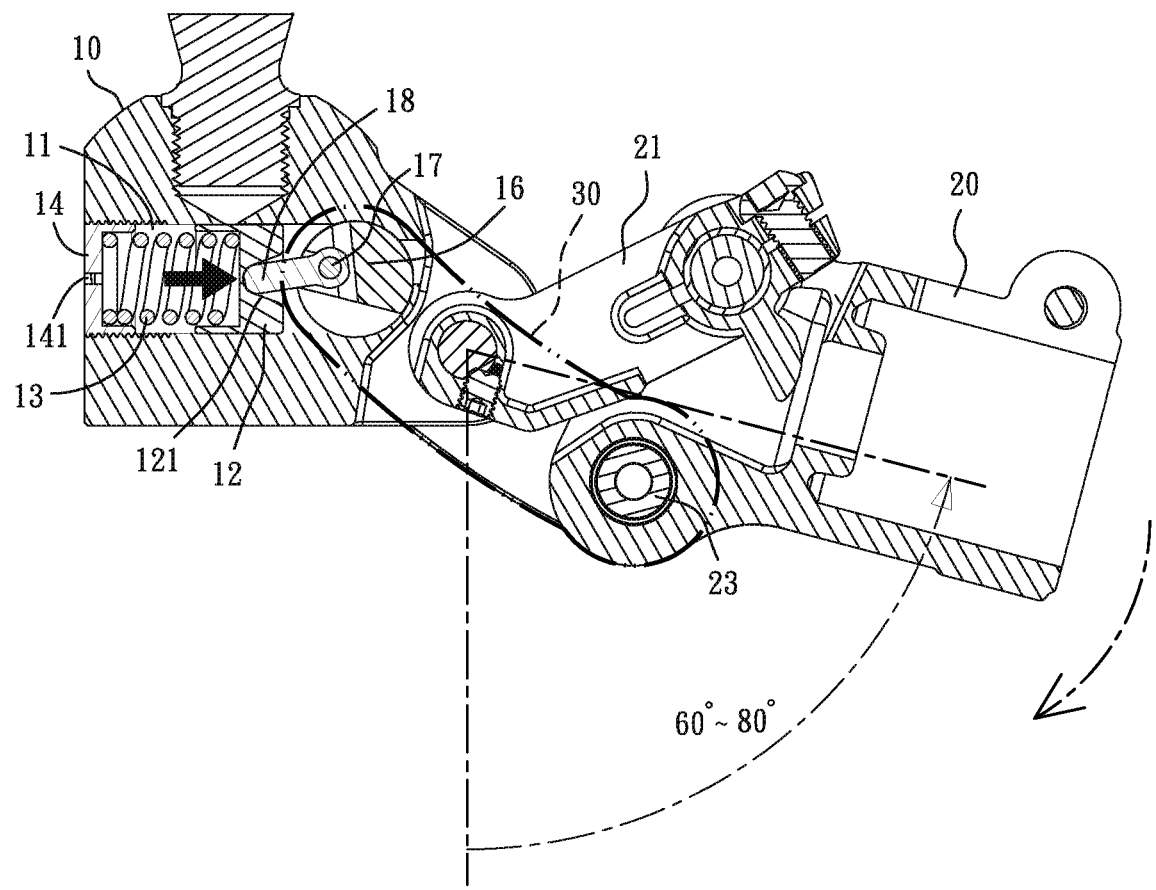
Figure 8:
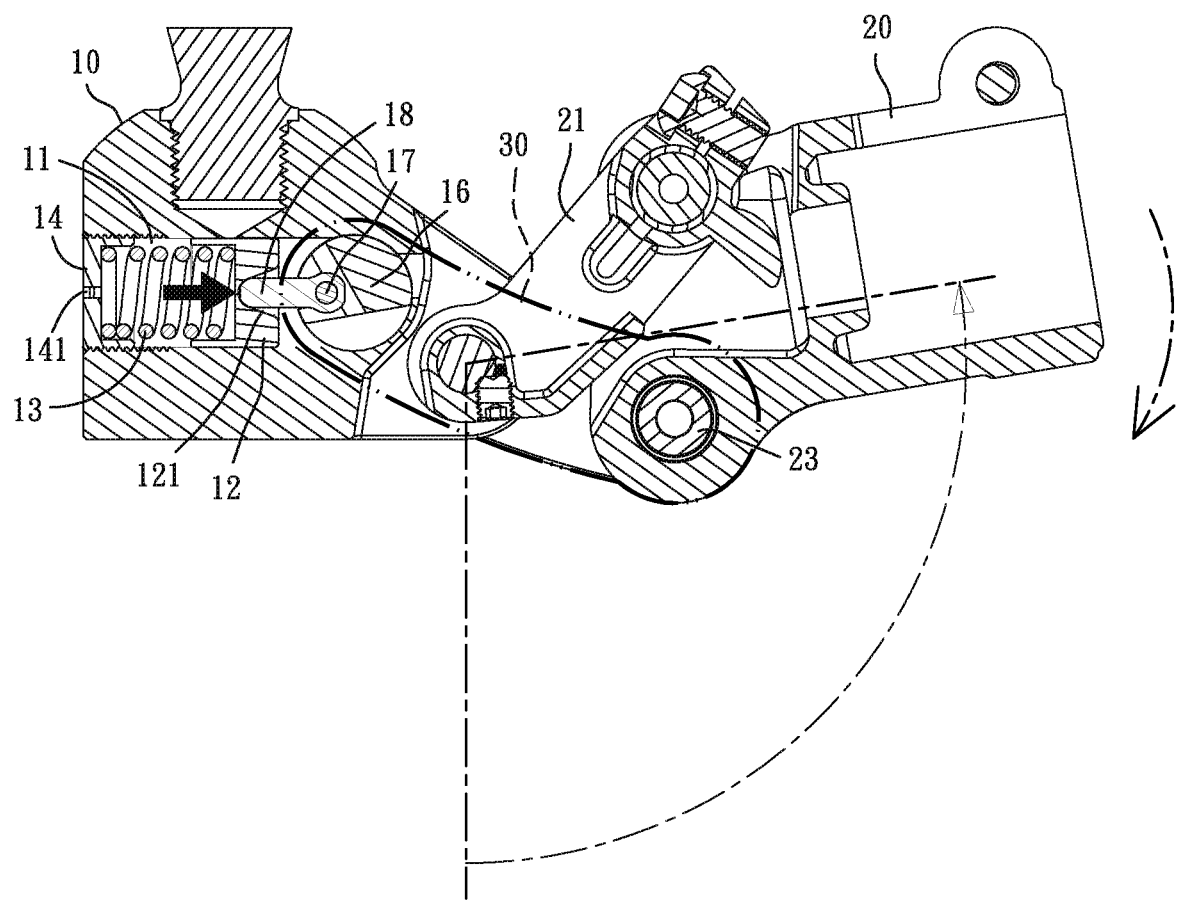

Referring to FIGS. 7 and 8, the knee joint of the present invention, when bending or curving, causes the transmission axle 16 to rotate by an angle, such that the push bar 18 pushes and compresses the elastic body 13 by means of the piston 12 to accumulate a spring force. The knee joint, when rotating in an opposite direction, is caused or assisted by the spring force of the elastic body 13 to return to an initial or original state. In other words, the spring force of the elastic body 13 pushes the push bar 18 in an opposite direction to have the transmission axle 16 rotate in an opposite direction and thus drive the curved plates 30 and the knee-joint body portion 20 to move in an opposite direction of the knee-joint head portion 10.

Figure 14:
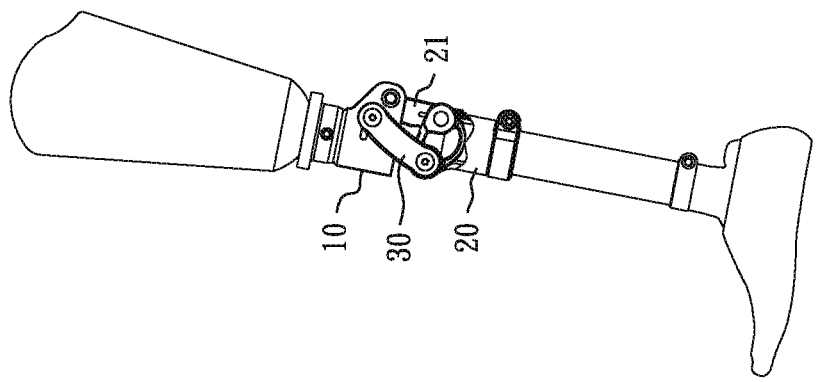
FIG. 14 illustrates an example of walking gait of the present invention, in which the middle part shows the bending angle is less than the critical angle in a fast walking gait, and the right-hand side part shows the walking gait returns to a straight state.
Figure 14:
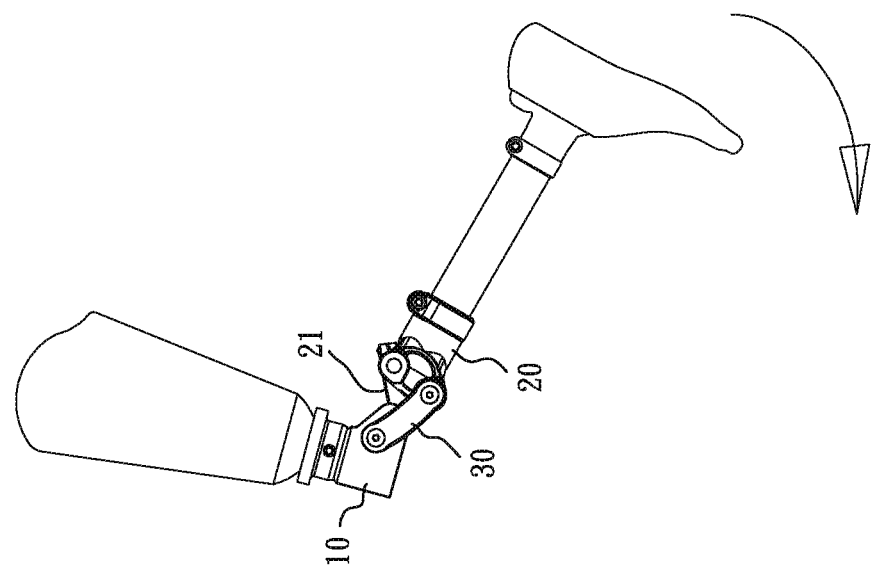
Figure 14:
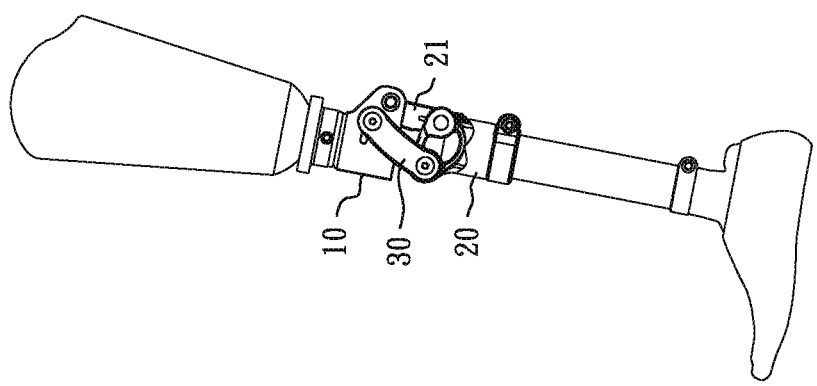
Figure 17:
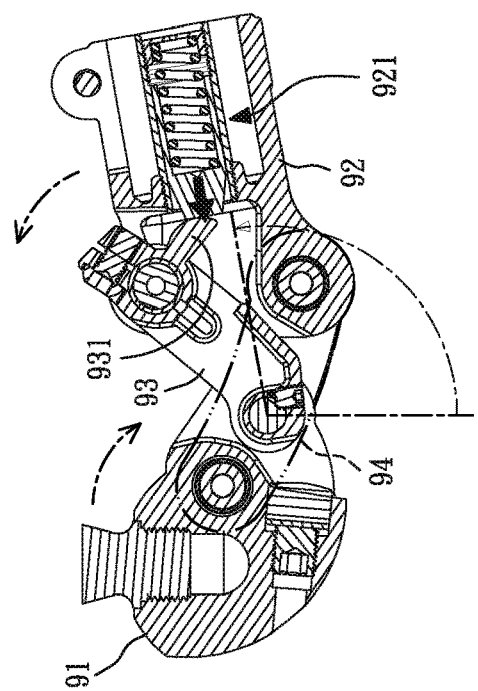
Figure 16:
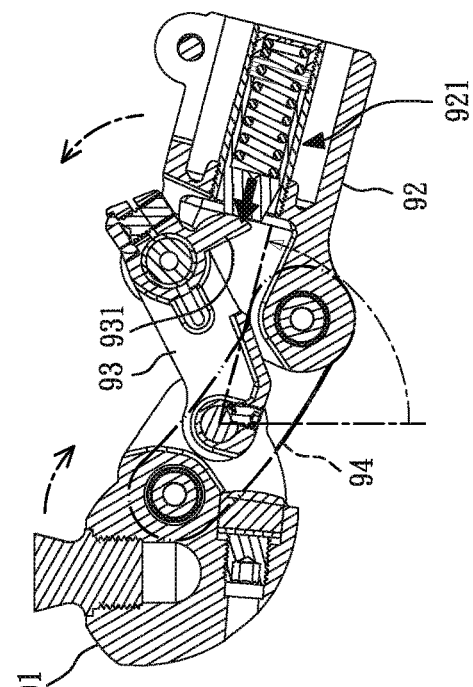
Figure 15:
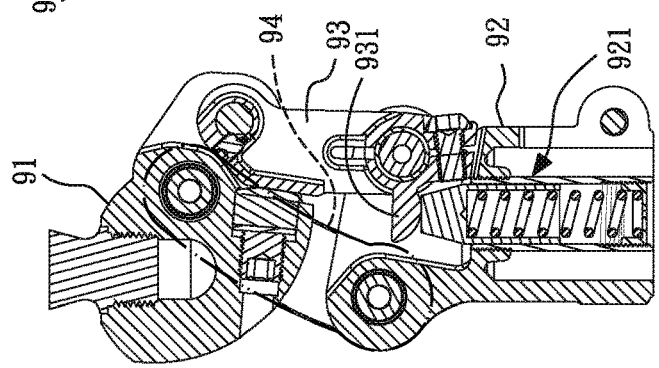
Figure 18:
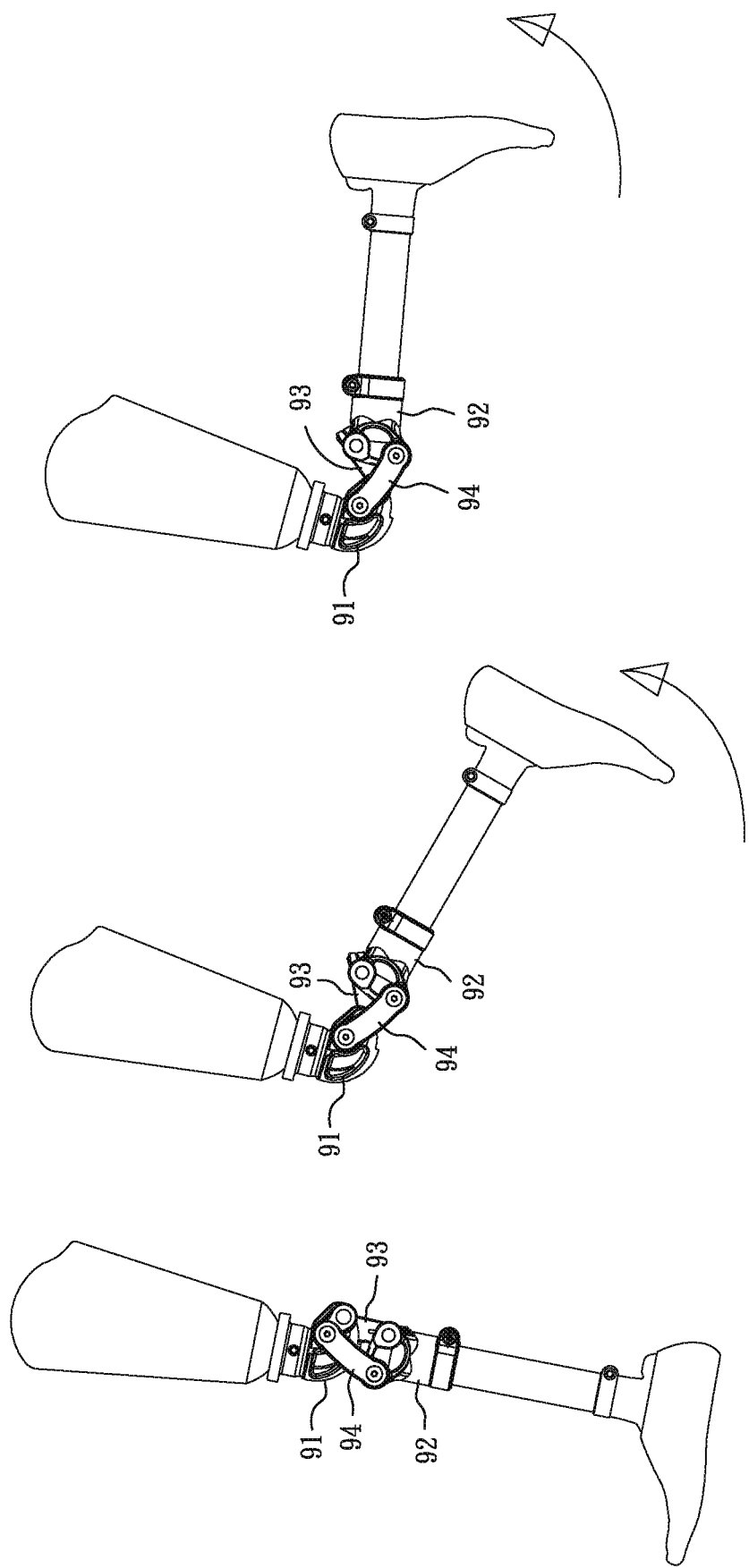
FIG. 18 illustrates an abnormal gait occurring in the prior art device, in which the middle part shows a bending angle is greater than the critical angle in a fast walking gait, and the right-hand side part shows the knee joint abnormally bends rearward in the walking gait.

By arranging a position-returning device and the push bar 18 in the knee-joint head portion 10, a critical angle of bending of the knee joint of the present invention can be set according to the position of the push-bar axle 17 on or relative to the transmission axle 16 and is preferably set at an angle that is greater than a maximum bending angle of walking by at least 20°. It is greater than the maximum angle of bending of walking (see FIG. 14), and this could ensure each step accomplished in a normal walking gait. As such, the present invention helps improve the drawback of a prior art knee joint of easily exceeding the critical angle after bending, which makes the knee joint that is supposed to get to a straight state continuously bending and causing tipping and hurting, and therefore enhances safety of operation.

Further, the location for adjusting the strength of the elastic body 13 is improved in order to allow adjustment of the strength to be carried out according to a walking speed of a user, allowing walking to be conducted with less effort.

Figure 9:
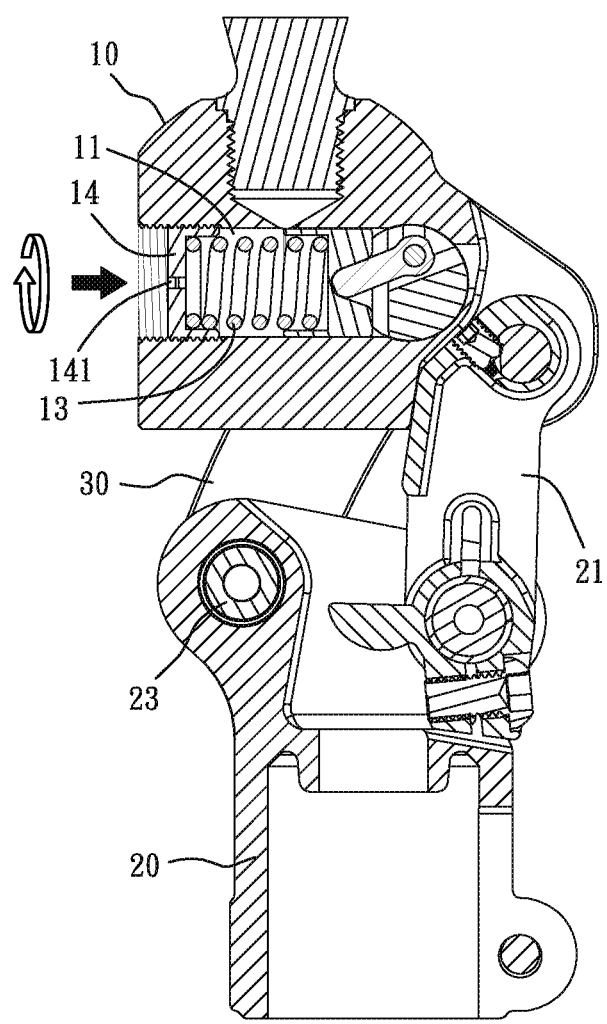
FIG. 9 is a cross-sectional view demonstrating an operation of adjusting a strength of an elastic body of the present invention.

Referring to FIGS. 1 and 9, in an embodiment, the adjustment cap 14 is screwed into and retained in the position-returning bore 11 and is formed with an adjustment slot 141. A user may insert a hand tool into the adjustment slot 141 to rotate the adjustment cap 14 for moving forward or backward in order to compress or release the elastic body 13 to achieve the purposes of adjusting the spring force.

Figure 10:
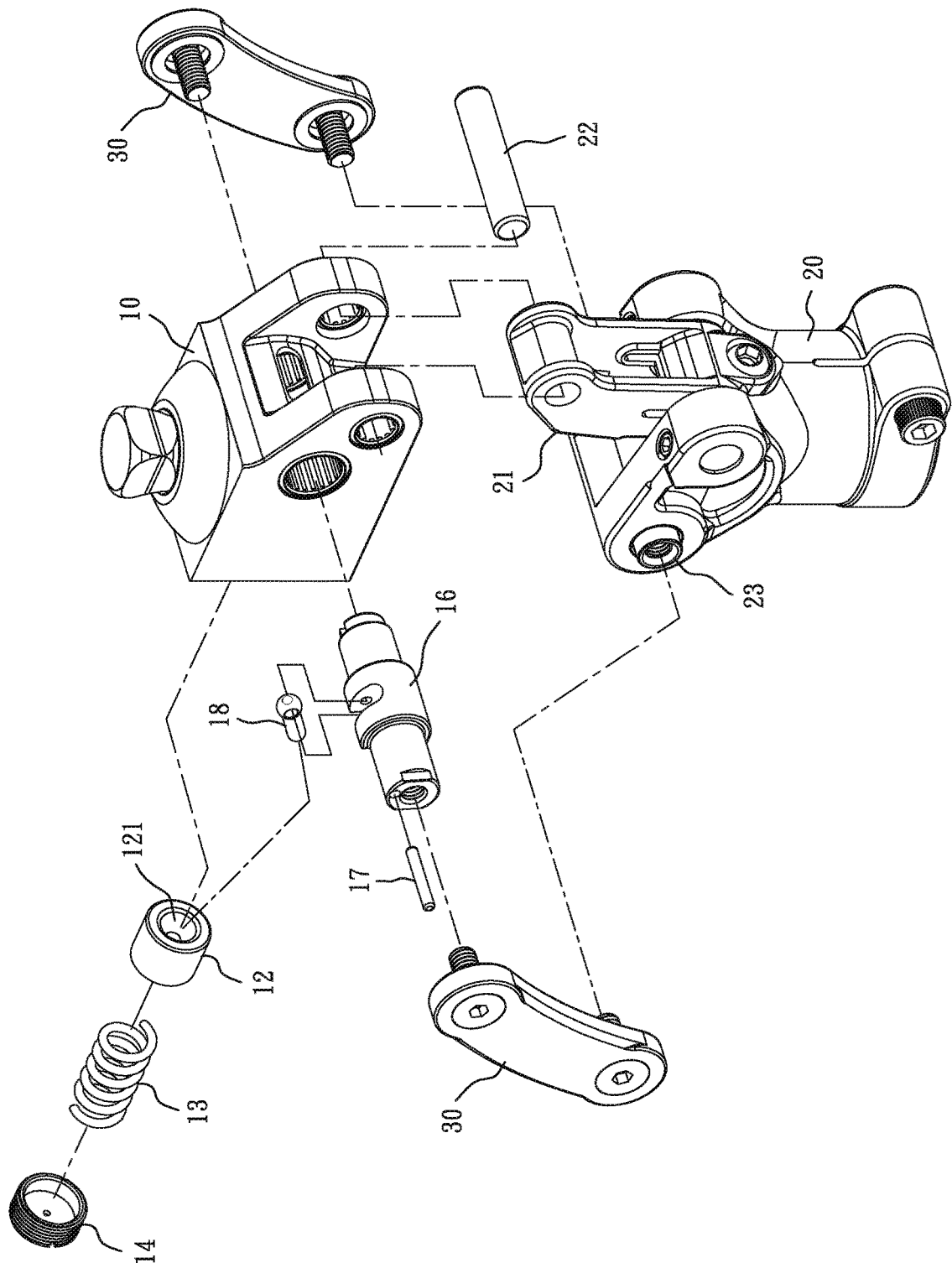
FIG. 10 is an exploded view showing a second embodiment of the present invention.

Referring to FIG. 10, in an embodiment, the push-bar axle 17 is arranged to extend through the transmission axle 16 and the push bar 18 in order to couple the transmission axle 16 and the push bar 18 together.

Figure 11:
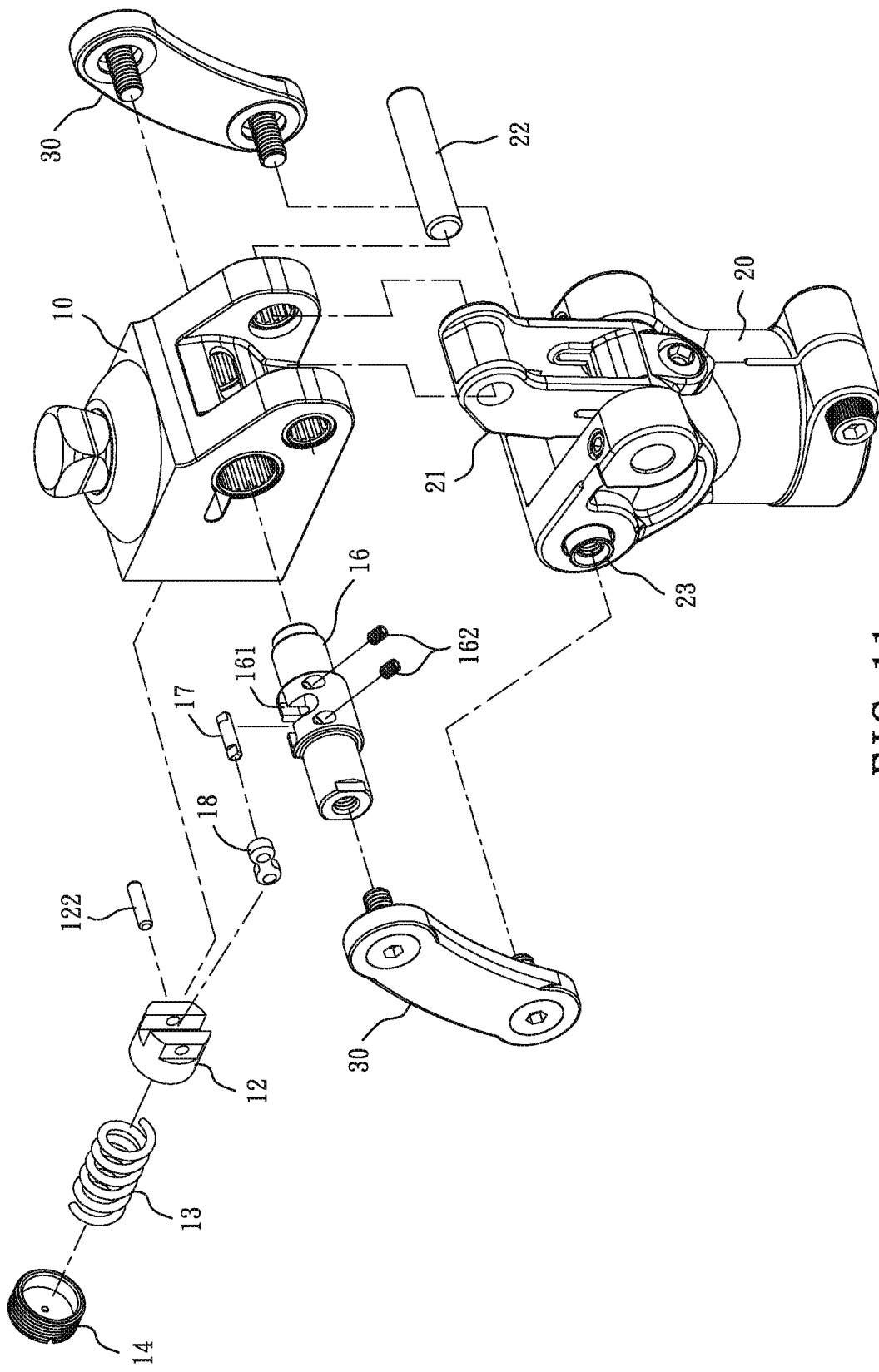
FIG. 11 is an exploded view showing a third embodiment of the present invention.
Figure 12:
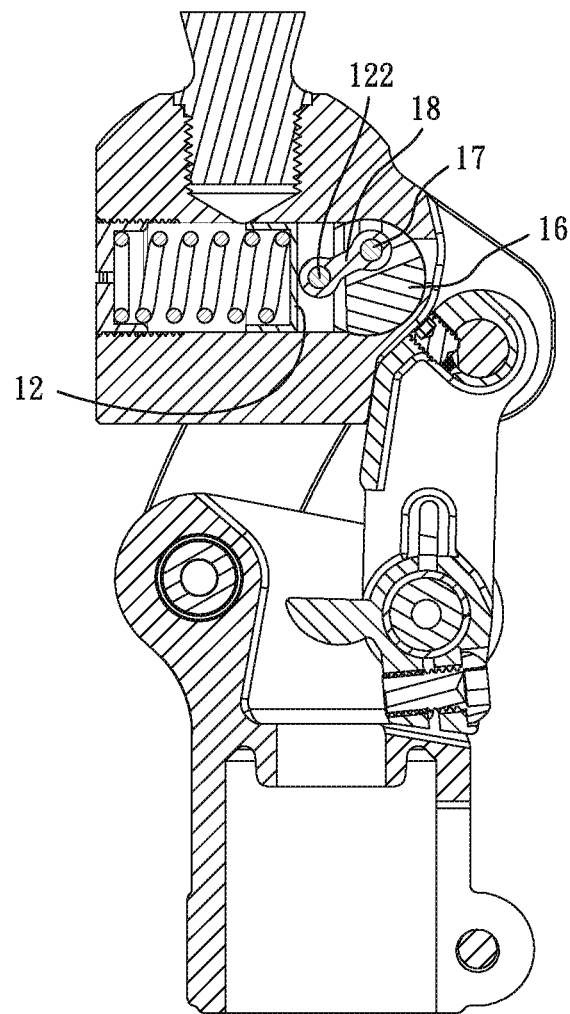
FIG. 12 is an exploded view showing a third embodiment of the present invention.
Figure 13:
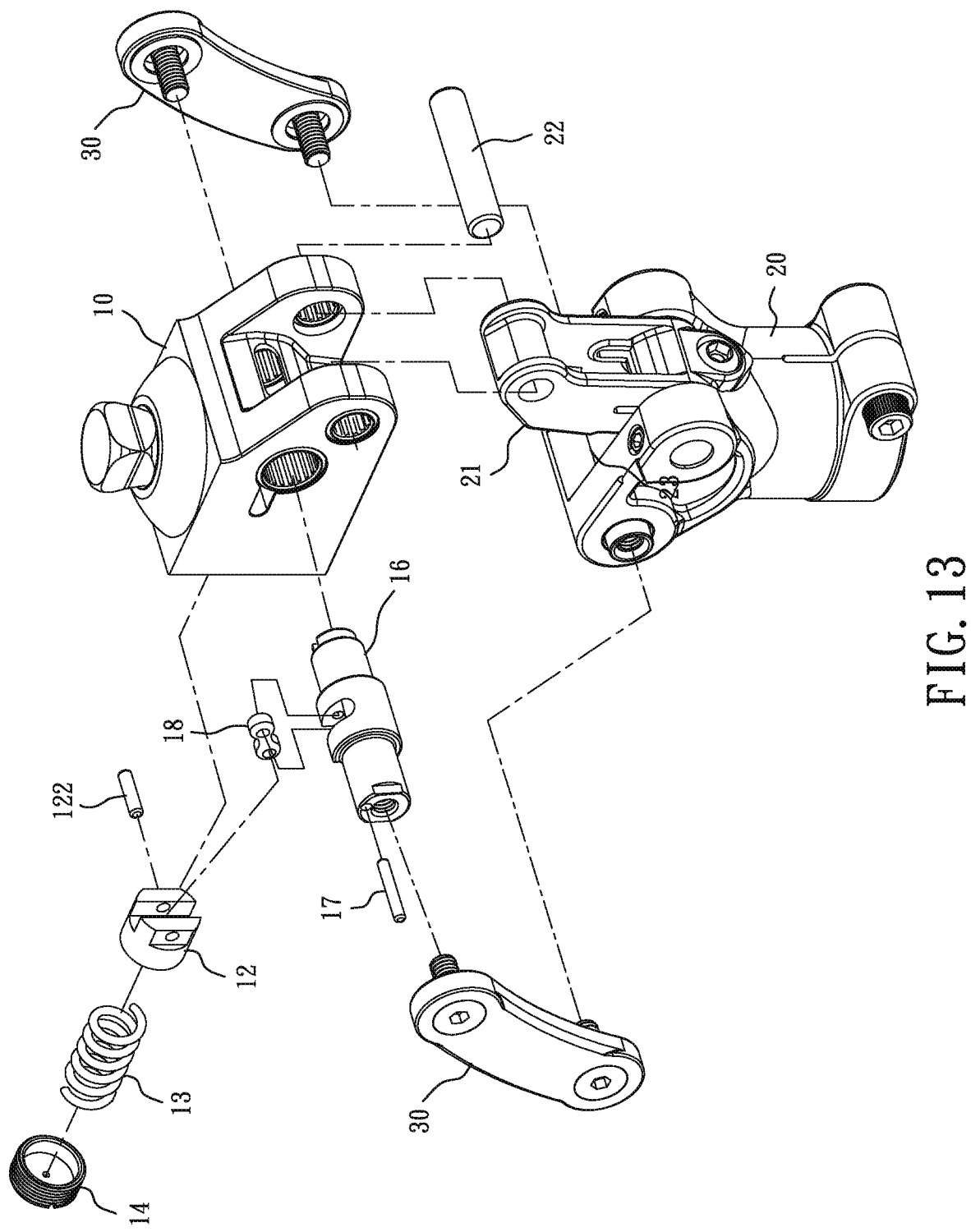
FIG. 13 is an exploded view showing a fourth embodiment of the present invention.

Referring to FIGS. 11-13, in an embodiment, the piston 12 is pivotally coupled to an end of the push bar 18 by a piston pin 122, so that the push bar 18 can stably push the piston 12 to prevent positional deviation during pushing.

I claim:

1. A knee joint structure, comprising:
a knee-joint head portion, which is formed with a position-returning bore, the position-returning bore receiving a piston, an elastic body, and an adjustment cap to arrange therein, the elastic body having two ends respectively supported on the piston and the adjustment cap, the knee-joint head portion being formed with an axle hole, the axle hole receiving a transmission axle to arrange therein, the transmission axle being formed with a notch, the notch receiving a push-bar axle to arrange therein, the push-bar axle being pivotally connected to a push bar that is operable to drive and move the piston;
a knee-joint body portion, which comprises a connection rod, the connection rod having an end that is pivotally connected, by a first shaft, to the knee joint head portion, the knee-joint body portion further comprising a second shaft; and
at least one curved plate, which has two ends that are respectively connected to the transmission axle and the second shaft.

2. The knee joint structure according to claim 1, wherein the piston is formed with a cavity, and the push bar has an end extended into and in contact engagement with the cavity.

3. The knee joint structure according to claim 1, wherein the transmission axle is provided with a bolt extending therein so that an end of the bolt is set in contact with the push-bar axle to fix the push-bar axle in the notch.

4. The knee joint structure according to claim 1, wherein the transmission axle has an end having a surface that is formed with a flat section to form an irregularly-shaped end configuration, the curved plate being formed with a retaining engagement trough, the retaining engagement trough being shaped to correspond to the irregular shape of the end configuration, the end of the transmission axle being set in and in mating and retaining engagement with the retaining engagement trough.

5. The knee joint structure according to claim 1, wherein the adjustment cap is screwed into and connected with the position-returning bore and is formed with an adjustment slot.

6. The knee joint structure according to claim 1, wherein the push-bar axle is arranged to extend through the transmission axle and the push bar in order to couple the transmission axle and the push bar together.

7. The knee joint structure according to claim 1, wherein the piston is pivotally coupled, by a piston pin, to an end of the push bar.

\* \* \* \* \*